US011104056B2

(12) United States Patent
Kurosaki et al.

(10) Patent No.: US 11,104,056 B2
(45) Date of Patent: Aug. 31, 2021

(54) BALLOON WRAPPING APPARATUS AND BALLOON WRAPPING METHOD

(71) Applicant: TERUMO KABUSHIKI KAISHA, Tokyo (JP)

(72) Inventors: Yasuo Kurosaki, Kanagawa (JP); Hiroshi Goto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 133 days.

(21) Appl. No.: 15/928,597

(22) Filed: Mar. 22, 2018

(65) Prior Publication Data
US 2018/0207855 A1  Jul. 26, 2018

Related U.S. Application Data

(63) Continuation of application No. PCT/JP2016/078036, filed on Sep. 23, 2016.

(30) Foreign Application Priority Data

Sep. 25, 2015  (JP) .............................. JP2015-188029

(51) Int. Cl.
B29C 53/08 (2006.01)
A61M 25/10 (2013.01)
(Continued)

(52) U.S. Cl.
CPC .......... B29C 53/08 (2013.01); *A61M 25/1029* (2013.01); *A61M 25/1038* (2013.01);
(Continued)

(58) Field of Classification Search
CPC ......... B29C 53/08; B29C 33/76; B29C 51/10; B29C 53/566; B29C 53/825;
(Continued)

(56) References Cited

U.S. PATENT DOCUMENTS 4,681,092 A * 7/1987 Cho ...................... A61M 25/10
600/18
5,350,361 A  9/1994 Tsukashima et al.
(Continued)

FOREIGN PATENT DOCUMENTS

CN  103660264 A  3/2014
CN  204379958 U  6/2015
(Continued)

OTHER PUBLICATIONS

Schrader et al., Manufacturing Processes & Materials, Society of Manufacturing Engineers, pp. 739-741, 2000. (Year: 2000).*
(Continued)

*Primary Examiner* — Michael N Orlando
*Assistant Examiner* — Christopher W Raimund
(74) *Attorney, Agent, or Firm* — Buchanan Ingersoll & Rooney PC

(57) ABSTRACT

A balloon wrapping apparatus and a balloon wrapping method are disclosed by which a balloon can be wrapped appropriately. The balloon wrapping apparatus for wrapping a balloon of a balloon catheter provided with the balloon at a distal portion of an elongated shaft includes: a pleating section that forms the balloon with wing shapes projecting in radial directions; a folding section that includes a plurality of blades aligned in a circumferential direction, and that folds the wing shapes formed in the balloon along the circumferential direction by moving rotationally the blades; and a rotational support portion that supports a portion of the shaft which portion is on a proximal side of the balloon, and that rotates the shaft in a direction opposite to a rotary movement direction of the blades in a state in which the balloon is positioned in relation to the folding section.

10 Claims, 12 Drawing Sheets

(51) Int. Cl.
  B29C 33/76 (2006.01)
  B29C 51/10 (2006.01)
  B29C 53/56 (2006.01)
  B29C 53/82 (2006.01)
  B29C 70/68 (2006.01)
  B29L 31/00 (2006.01)

(52) U.S. Cl.
  CPC .............. B29C 33/76 (2013.01); B29C 51/10 (2013.01); B29C 53/566 (2013.01); B29C 53/825 (2013.01); B29C 70/682 (2013.01); B29L 2031/7543 (2013.01)

(58) Field of Classification Search
  CPC ............. B29C 70/682; A61M 25/1038; A61M 25/1029; B29L 2031/7543
  See application file for complete search history.

(56) References Cited

U.S. PATENT DOCUMENTS

| | | | |
|---|---|---|---|
| 5,893,852 A * | 4/1999 | Morales | A61F 2/958 606/108 |
| 7,762,804 B1 | 7/2010 | Stupecky | |
| 2001/0037140 A1 | 11/2001 | Gaudoin et al. | |
| 2002/0163104 A1* | 11/2002 | Motsenbocker | A61M 25/1002 264/320 |
| 2004/0123437 A1* | 7/2004 | Kokish | B25B 27/146 29/235 |
| 2010/0040766 A1* | 2/2010 | Chappa | B05D 1/02 427/2.3 |
| 2012/0042501 A1* | 2/2012 | Wang | A61F 2/95 29/505 |
| 2013/0197563 A1* | 8/2013 | Saab | A61M 29/02 606/191 |
| 2013/0310913 A1* | 11/2013 | Wang | A61F 2/958 623/1.11 |
| 2014/0100592 A1* | 4/2014 | Burton | A61M 25/1038 606/159 |
| 2014/0319750 A1 | 10/2014 | Yanes et al. | |

FOREIGN PATENT DOCUMENTS

| | | |
|---|---|---|
| JP | H08-098893 A | 4/1996 |
| JP | 2002-512862 A | 5/2002 |
| JP | 2004-525704 A | 8/2004 |
| JP | 2006-271678 A | 10/2006 |
| JP | 2013-056071 A | 3/2013 |
| JP | 2013056071 A * | 3/2013 |
| JP | 2014-018493 A | 2/2014 |
| JP | 5930528 B2 | 6/2016 |
| WO | WO-2014076776 A1 * | 5/2014 |

OTHER PUBLICATIONS

The extended European Search Report dated Mar. 18, 2019, by the European Patent Office in corresponding European Patent Application No. 16848666.0-1132. (5 pages).

International Search Report (PCT/ISA/210) dated Dec. 20, 2016, by the Japanese Patent Office as the International Searching Authority for International Application No. PCT/JP2016/078036.

Written Opinion (PCT/ISA/237) dated Dec. 20, 2016, by the Japanese Patent Office as the International Searching Authority for International Application No. PCT/JP2016/078036.

English translation of International Search Report issued in International Patent Application No. PCT/JP2016/078036, 2 pages (dated Dec. 20, 2016).

English translation of Written Opinion issued in International Patent Application No. PCT/JP2016/078036, 4 pages (dated Dec. 20, 2016).

Office Action (The First Office Action) and Search Report dated Jun. 5, 2020, by the State Intellectual Property Office of People's Republic of China in corresponding Chinese Patent Application No. 201680055259.3 and an English translation of the Office Action. (14 pages).

An English Translation of the Office Action (Advisory Action) dated Sep. 28, 2020, by the Japanese Patent Office in corresponding Japanese Patent Application No. 2017-540919. (5 pages).

* cited by examiner

FIG. 9
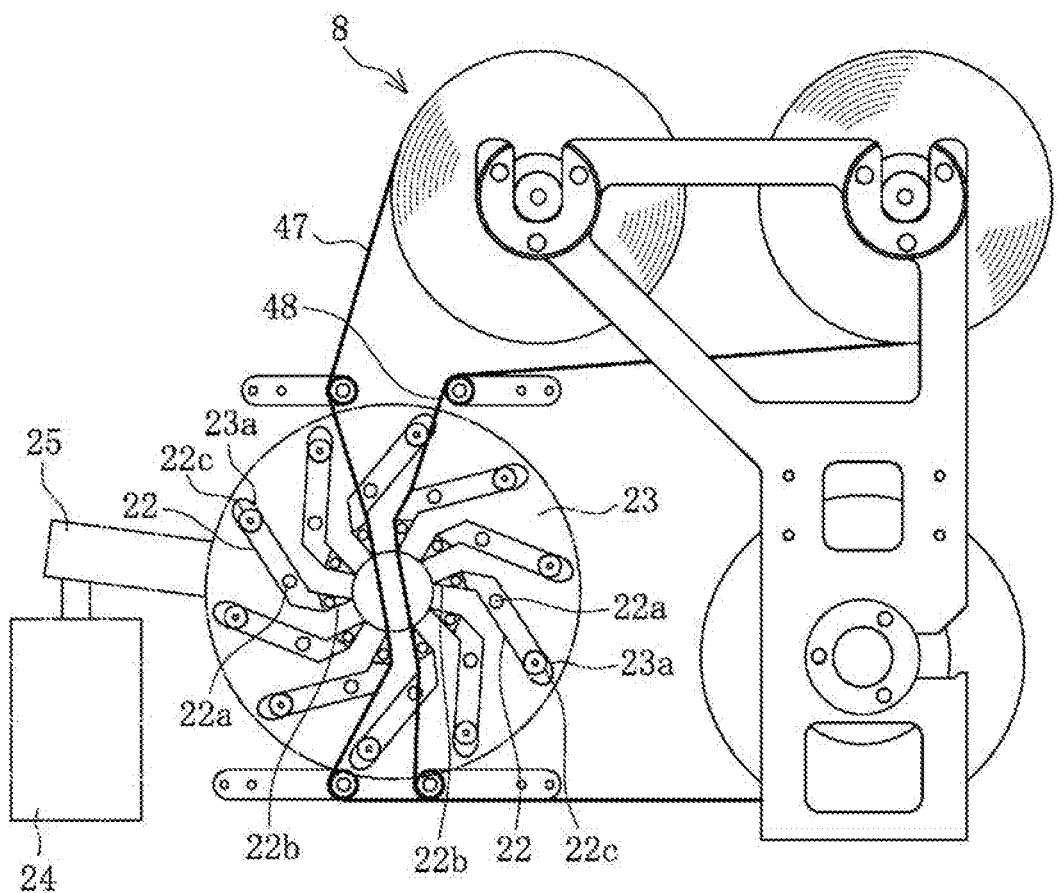
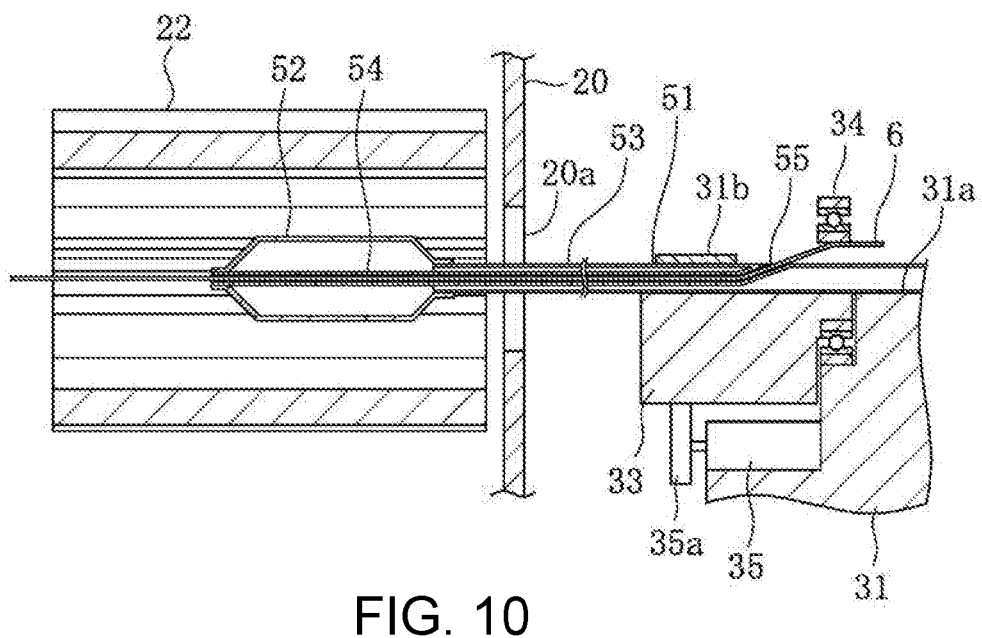
FIG. 10

Table 1

| Conditions | Example 1 | Comparative Example 1 | Comparative Example 2 | Example 2 | Example 3 |
|---|---|---|---|---|---|
| Diameter/length of balloon | 2.0 mm/40 mm | 4.0 mm/200 mm | 3.0 mm/200 mm | 2.0 mm/200 mm | 6.0 mm/200 mm |
| Material of balloon | Nylon | Nylon | Nylon | Nylon | Nylon |
| Surface condition of balloon catheter | Smooth, non-porous | Smooth, non-porous | Smooth, non-porous | Smooth, non-porous | Smooth, non-porous |
| Amount of paclitaxel | 3.2 µg/mm$^2$ | 3.6 µg/mm$^2$ | 3.6 µg/mm$^2$ | 3.2 µg/mm$^2$ | 3.2 µg/mm$^2$ |
| Diameter/length of core metal member | 0.39 mm/700 mm | 0.38 mm/500 mm | 0.38 mm/500 mm | 0.38 mm/700 mm | 0.48 mm/700 mm |
| Shape of core metal member | Wire-like | Wire-like | Wire-like | Wire-like | Wire-like |
| Material of core metal member | SUS | SUS | SUS | SUS | SUS |
| Material of holding portion | Silicone rubber | Silicone rubber | Silicone rubber | Silicone rubber | Silicone rubber |
| Shape/function of distal support of pleating section | Insertion into distal support | Insertion into distal support | Insertion into distal support | Insertion into distal support | Insertion into distal support |
| Number of blades in pleating section | Three | Three | Three | Three | Four |
| Characteristics of films | Difficult to electrostatically charge, smooth | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm | Teflon/0.001 mm |
| Control of pulling by collet chuck | - | - | - | - | - |
| Shape/function of distal support of folding section | Insertion into central portion of distal support | Insertion into central portion of distal support | Insertion into central portion of distal support | Insertion into central portion of distal support | Insertion into central portion of distal support |
| Number of blades in folding section | Ten | Ten | Ten | Ten | Ten |
| Control of pulling by collet chuck | - | - | - | - | - |
| Timing of start of rotation | Point of time when films contacted wings | - | - | Point of time when films contacted wings | - |
| Rotation of balloon catheter as viewed from proximal side | Counterclockwise | - | - | Counterclockwise | - |

FIG. 16

Table 2

| Conditions | Example 3 | Example 4 | Example 5 | Example 6 |
|---|---|---|---|---|
| Diameter/length of balloon | 6.0 mm/200 mm | 4.0 mm/200 mm | 4.0 mm/200 mm | 4.0 mm/200 mm |
| Material of balloon | Nylon | Nylon | Nylon | Nylon |
| Surface condition of balloon catheter | Smooth, non-porous | Smooth, non-porous | Smooth, non-porous | Smooth, non-porous |
| Amount of paclitaxel | 3.2 µg/mm$^2$ | 3.2 µg/mm$^2$ | 3.2 µg/mm$^2$ | 3.2 µg/mm$^2$ |
| Diameter/length of core metal member | 0.48 mm/700 mm | 0.48 mm/700 mm | 0.48 mm/700 mm | 0.48 mm/700 mm |
| Shape of core metal member | Wire-like | Hollow | Hollow | Hollow |
| Material of core metal member | SUS | SUS | SUS | SUS |
| Material of holding portion | Silicone rubber | Silicone rubber | Silicone rubber | Silicone rubber |
| Shape/function of distal support of pleating section | Clamping in collet chuck | Clamping in collet chuck | Clamping in collet chuck | Clamping in collet chuck |
| Number of blades in pleating section | Four | Four | Four | Four |
| Characteristics of films | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Shape/function of distal support of folding section | Clamping in collet chuck | Clamping in collet chuck | Clamping in collet chuck | Clamping in collet chuck |
| Number of blades in folding section | Eight | Twelve | Twelve | Twelve |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Timing of start of rotation | Point of time when films contacted wings | Point of time when films contacted wings | Point of time when films contacted wings | Point of time when films contacted wings |
| Rotation of balloon catheter as viewed from proximal side | Counterclockwise | Counterclockwise | Counterclockwise | Counterclockwise |

FIG. 17

Table 3

| Conditions | Example 7 | Comparative Example 4 | Comparative Example 5 | Comparative Example 6 |
|---|---|---|---|---|
| Diameter/length of balloon | 3.0 mm/20 mm | 4.0 mm/200 mm | 3.0 mm/200 mm | 2.0 mm/200 mm |
| Material of balloon | Nylon elastomer | Nylon | Nylon | Nylon |
| Surface condition of balloon catheter | Smooth, non-porous | Smooth, non-porous | Smooth, non-porous | Smooth, non-porous |
| Amount of paclitaxel | 3.2 μg/mm$^2$ | 3.6 μg/mm$^2$ | 3.6 μg/mm$^2$ | 3.2 μg/mm$^2$ |
| Diameter/length of core metal member | 0.38 mm/500 mm | 0.38 mm/500 mm | 0.38 mm/500 mm | 0.38 mm/700 mm |
| Shape of core metal member | Wire-like | Wire-like | Wire-like | Wire-like |
| Material of core metal member | SUS | SUS | SUS | SUS |
| Material of holding portion | Silicone rubber | Silicone rubber | Silicone rubber | Silicone rubber |
| Shape/function of distal support of pleating section | Insertion into distal support | Insertion into distal support | Insertion into distal support | Clamping in collet chuck |
| Number of blades in pleating section | Three | Three | Three | Four |
| Characteristics of films | Difficult to electrostatically charge, smooth | - | - | Difficult to electrostatically charge, smooth |
| Film (material/thickness) | Teflon/0.001 mm | None | None | Teflon/0.001 mm |
| Control of pulling by collet chuck | - | - | - | - |
| Shape/function of distal support of folding section | Insertion into distal support | Insertion into distal support | Insertion into distal support | Insertion into distal support |
| Number of blades in folding section | Twelve | Ten | Ten | Ten |
| Control of pulling by collet chuck | - | - | - | - |
| Timing of start of rotation | Point of time when films contacted wings | - | - | - |
| Rotation of balloon catheter as viewed from proximal side | Counterclockwise | - | - | - |

FIG. 18

Table 4

| Examples | Presence/absence of films | Size (diameter/length) of balloon | Amount of paclitaxel per unit area [μg/mm$^2$] | | Retention rate of paclitaxel (%) |
|---|---|---|---|---|---|
| | | | After Coating | After folding | |
| Example 1 | Present | 2.0 mm/40 mm | 3.2 | 2.8 | 88 |
| Comparative Example 1 | Present | 4.0 mm/200 mm | 3.6 | 3.5 | 97 |
| Comparative Example 2 | Present | 3.0 mm/200 mm | 3.6 | 3.3 | 92 |
| Example 2 | Present | 2.0 mm/200 mm | 3.2 | 3.1 | 96 |
| Comparative Example 3 | Present | 6.0 mm/200 mm | 3.2 | 3.1 | 97 |
| Comparative Example 4 | Absent | 4.0 mm/200 mm | 3.6 | 2.8 | 78 |
| Comparative Example 5 | Absent | 3.0 mm/200 mm | 3.6 | 2.6 | 72 |

FIG. 19

Table 5

| Examples | Rotation of balloon during folding | Number of drug-coated balloons in which back folding was generated [(Number of drug-coated balloons in which back folding was generated)/(Total number of drug-coated balloons subjected to folding)] | Generation rate of back folding [%] |
|---|---|---|---|
| Example 2 | Performed | 1/142 | 0.7 |
| Comparative Example 6 | Not performed | 22/46 | 48 |

FIG. 20

BALLOON WRAPPING APPARATUS AND BALLOON WRAPPING METHOD

CROSS-REFERENCES TO RELATED APPLICATIONS

This application is a continuation of International Application No. PCT/JP2016/078036 filed on Sep. 23, 2016, which claims priority to Japanese Application No. 2015-188029 filed on Sep. 25, 2015, the entire contents of both of which are incorporated herein by reference.

TECHNICAL FIELD

The present disclosure relates to a balloon wrapping apparatus and a balloon wrapping method for wrapping a balloon of a balloon catheter.

BACKGROUND DISCUSSION

Treatment of a lesion of a blood vessel by use of a catheter has been widely practiced because of little surgical invasiveness. For example, in percutaneous coronary angioplasty (Percutaneous Transluminal Coronary Angioplasty), a balloon catheter can be used for improving blood flow by pushing open a lesion part of a coronary artery. In general, a balloon catheter includes an elongated hollow shaft, a balloon provided on the distal side of the shaft, and a hub provided on the proximal side of the shaft. The balloon catheter may be provided with a drug eluting balloon having a surface coated with a drug.

The balloon of a balloon catheter is required to be as small as possible in diameter when deflated, for good passing properties in a blood vessel. The balloon is formed in a small diameter form by being wrapped at the time of manufacturing the catheter. The wrapping of the balloon is conducted by a pleating step of bending the balloon to form a plurality of wing shapes, for example, three or four wing shapes in the circumferential direction, and a folding step of folding the thus formed wing shapes toward one side in the circumferential direction.

As a conventional balloon wrapping apparatus, there may be mentioned, for example, the one described in JP-T-2004-525704. The balloon wrapping apparatus has a pleating section for performing pleating, and a folding section for performing folding. In addition, the balloon wrapping apparatus has a support base which supports the shaft of the balloon catheter and which is slidable such that the balloon can be inserted into each head.

The pleating section has a plurality of blades in the circumferential direction for shaping the balloon to have the wings. Between the plurality of blades, a space part extending along an insertion direction of the balloon is formed. In addition, the blades can be moved rotationally in such a manner as to change the shape of the space part. The balloon is inserted into the space part between the blades, and the balloon is narrowed by the blades moved rotationally, whereby wing shapes are formed.

The folding section has a plurality of blades movable rotationally such that the wing shapes formed in the balloon can be folded in the manner of being laid flat along the circumferential direction. The balloon is inserted into a region surrounded by the plurality of blades, and the blades are moved rotationally such as to close the region between the blades, whereby the wing shapes formed in the balloon are folded along the circumferential direction.

When wrapping the balloon, the balloon catheter is placed on the support base, and the support base is slid toward the pleating section, whereby the balloon is advanced into the pleating section, and pleating is conducted. When the balloon is drawn out of the pleating section, the balloon is subsequently advanced into the folding section, and folding is conducted.

SUMMARY

For improving the passing property of the balloon, wrapping of the balloon should be conducted in such a manner that the wing shapes are formed in accurate shapes at predetermined intervals in the circumferential direction. However, in folding, the inclination directions of the wing shapes may become out of order, possibly resulting in back folding in which the wing shapes are folded in a reverse direction in the circumferential direction.

A balloon wrapping apparatus and a balloon wrapping method are disclosed by which a balloon can be wrapped appropriately.

A balloon wrapping apparatus is disclosed for wrapping a balloon of a balloon catheter provided with the balloon at a distal portion of an elongated shaft, the balloon wrapping apparatus including: a pleating section that forms the balloon with wing shapes projecting in radial directions; a folding section that includes a plurality of folding members aligned in a circumferential direction, and that folds the wing shapes formed in the balloon along the circumferential direction by moving rotationally the folding members; and a rotational support portion that supports a portion of the shaft which portion is on a proximal side of the balloon, and that rotates the shaft in a direction opposite to a rotary movement direction of the folding members in a state in which the balloon is positioned in relation to the folding section.

A balloon wrapping method is disclosed for wrapping a balloon of a balloon catheter provided with the balloon at a distal portion of an elongated shaft, the balloon wrapping method including: a step of forming the balloon with wing shapes projecting in radial directions; a step of disposing the balloon formed with the wing shapes at a central area of a plurality of folding members aligned in a circumferential direction and putting the folding members into contact with the wing shapes of the balloon; a step of rotating the shaft in a direction reverse to a rotary movement direction of the folding members; and a step of moving rotationally the folding members to fold the wing shapes formed in the balloon along the circumferential direction.

In accordance with an exemplary embodiment, the balloon wrapping apparatus configured as above has the rotational support portion that rotates the shaft in the direction opposite to the rotary movement direction of the folding members. Therefore, it is possible, by rotating the balloon, to align the directions of the wing shapes in one direction. For this reason, the folding directions become stable at the time of folding the wing shapes in the folding section, so that back folding can be restrained from occurring, and the balloon can be wrapped appropriately.

Where the rotational support portion has a holding portion that holds the shaft, the shaft can be held and the shaft can be rotated stably. Therefore, generation of back folding in the folding section can be restrained more securely, and the balloon can be wrapped appropriately.

Where the balloon wrapping apparatus has a core metal member to be inserted in the shaft, bending of the shaft rotated by the rotational support portion can be restrained, and the rotation can be stabilized. Therefore, the balloon can be wrapped appropriately.

In addition, in the balloon wrapping method configured as above, the shaft is rotated in the direction opposite to the rotary movement direction of the folding members, and, further, the folding members are moved rotationally to thereby fold the wing shapes of the balloon. Therefore, the directions of the wing shapes can be aligned in one direction. For this reason, the directions in which the wing shapes are folded by the folding members are made stable, whereby generation of back folding can be restrained, and the balloon can be wrapped appropriately.

Where the folding members are moved rotationally to thereby put the folding members into contact with the wing shapes of the balloon in the step of putting the folding members into contact with the wing shapes of the balloon, the folding members can be reliably put into contact with the wing shapes of the balloon. At the time of rotating the shaft in the direction reverse to the rotary movement direction of the folding members, therefore, the directions of the wing shapes of the balloon can be aligned relatively assuredly.

Where the folding members are moved rotationally, while rotating the shaft in the direction reverse to the rotary movement direction of the folding members, so as thereby to fold the wing shapes formed in the balloon along the circumferential direction, the directions in which the wing shapes are folded by the folding members are made stable, so that generation of back folding can be restrained more securely, and the balloon can be wrapped appropriately.

A balloon wrapping apparatus is disclosed for wrapping a balloon of a balloon catheter provided with the balloon at a distal portion of an elongated shaft, the balloon wrapping apparatus comprising: a pleating section configured to form the balloon with wing shapes projecting in radial directions; a folding section that includes a plurality of blades aligned in a circumferential direction, and configured to fold the wing shapes formed in the balloon along the circumferential direction by moving rotationally the blades; and a rotational support portion configured to support a portion of the shaft which portion is on a proximal side of the balloon, and to rotate the shaft in a direction opposite to a rotary movement direction of the blades in a state in which the balloon is positioned in relation to the folding section.

BRIEF DESCRIPTION OF THE DRAWINGS

FIG. 9 is a front view depicting the layout of blades in a folding section and the film supplying section.

FIG. 10 is a sectional view of a balloon catheter disposed in the folding section.

FIGS. 16-18 are Tables 1-3, which illustrate examples of the present disclosure and comparative examples as disclosed herein, which includes drug-coated balloons of Examples 1 to 7 and Comparative Examples 1 to 6 produced under the conditions as set forth in Tables 1-3.

FIG. 19 is Table 4, which compares Examples 1 and 2, and Comparative Examples 1-5 to one another including amounts of paclitaxel per unit area after coating and after folding, and a retention rate of paclitaxel for each of the Examples.

FIG. 20 is Table 5, which depicts the number of drug-coated balloons in which back folding was generated, the total number of drug-coated balloons subjected to folding, and generation rate of back folding for Example 2 and Comparative Example 6.

DETAILED DESCRIPTION

Figure 1:
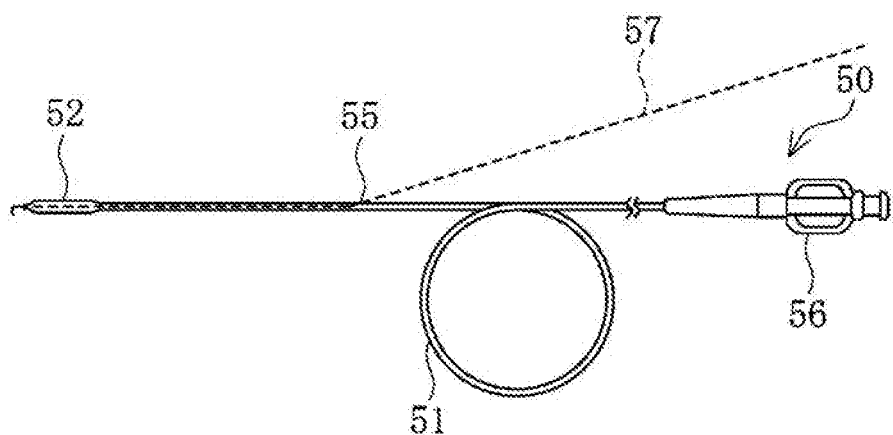
FIG. 1 is a front view of a rapid exchange type balloon catheter.

An exemplary embodiment of the present invention will be described below, referring to the drawings. Note that the dimensional ratios in the drawings may be exaggerated and be different from the actual ratios, for convenience of explanation. Herein, the side of insertion of a balloon catheter 50 into a body lumen will be referred to as "distal end" or "distal side," and the side of an operator's hand operation will be referred to as "proximal end" or "proximal side."

A balloon wrapping apparatus according to the present embodiment is an apparatus capable of wrapping a balloon so as to wrap the balloon around a shaft, at the time of manufacturing a balloon catheter having a balloon at a distal portion of an elongated shaft.

The balloon catheter to be wrapped may be subjected to hydrophilic coating for the purpose of improving properties for delivery to a lesion part, or may have a balloon surface subjected to a surface treatment such as a plasma treatment or irradiation with UV rays, but this is not particularly restrictive. There can also be used a balloon catheter in which the surface of a balloon has been subjected to a drug coating for delivery of a drug to a lesion part.

Figure 2:
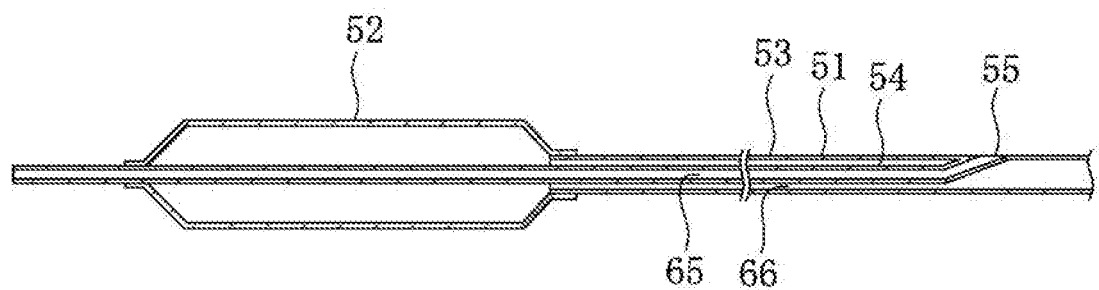
FIG. 2 is a sectional view of a distal portion of the balloon catheter.

In the first place, a balloon catheter 50 will be described. As depicted in FIGS. 1 and 2, the balloon catheter 50 includes an elongated hollow shaft 51, a balloon 52 provided at a distal-side end portion of the shaft 51, and a hub 56 secured to a proximal-side end portion of the shaft 51. The length of the balloon 52 in a major axis direction is not particularly limited, and, for example, is greater than approximately 3 mm. Preferably, the length of the balloon in the major axis direction, for example, is approximately 20 mm to 400 mm, more preferably 30 mm to 300 mm, and further preferably approximately 40 mm to 200 mm.

The diameter of the balloon 52 in a minor axis direction (the direction orthogonal to the major axis direction) is not particularly restricted, and, for example, is preferably not less than 1 mm, more preferably 1 mm to 10 mm, still more preferably 2 mm to 8 mm, and further preferably 2 mm to 4 mm. The material of the balloon 52 is not specifically restricted so long as it is flexible, and is composed, for example, of one or more of polyamides and polyamide elastomers. The surface of the balloon 52 preferably has a smooth surface, but it may not necessarily be smooth. The surface of the balloon 52 may have minute (extremely small) pores that do not penetrate the film, but may not necessarily have minute pores.

The shaft 51 includes a hollow outer tube 53 and a hollow inner tube 54. The inner tube 54 is accommodated in the hollow inside of the outer tube 53, and the shaft 51 has a double-tube structure at its distal portion. The hollow inside of the inner tube 54 forms a guide wire lumen 65 in and through which a guide wire 57 is to be inserted and passed. In addition, an inflation lumen 66 through which an inflation fluid for the balloon 52 is permitted to flow is formed in the hollow inside of the outer tube 53 and on the outside of the inner tube 54. The inner tube 54 is open to the exterior at an opening portion 55.

The inner tube 54 protrudes to the distal side beyond a distal end of the outer tube 53. The balloon 52 has a proximal-side end portion fixed to a distal portion of the outer tube 53, and has a distal-side end portion fixed to a distal portion of the inner tube 54. As a result of this, the inside of the balloon 52 communicates with the inflation lumen 66. The balloon 52 can be inflated by injecting an inflation fluid into the balloon 52 through the inflation lumen 66. The inflation fluid may be either a gas or a liquid; for example, a gas such as helium gas, $CO_2$ gas and $O_2$ gas or a liquid such as a saline solution and a contrast medium can be used as the inflation fluid.

The outer tube 53 and the inner tube 54 are preferably formed from a material that has a certain degree of flexibility. Examples of such a material include polyolefins such as polyethylene, polypropylene, polybutene, ethylene-propylene copolymer, ethylene-vinyl acetate copolymer, ionomers, or mixtures of two or more of them, flexible polyvinyl chloride resin, polyamides, polyamide elastomers, polyesters, polyester elastomers, polyurethane, fluoro-resin such as polytetrafluoroethylene, silicone rubbers, and latex rubbers.

Where the balloon catheter 50 is used in such a manner that the elongated shaft 51 of the balloon catheter 50 is inserted into a body organ and the balloon 52 provided on the distal side thereof is inflated at a lesion part, it is possible to push open the lesion part and thereby to perform a treatment. The shaft 51 is provided, at a position near the distal side thereof, with the opening portion 55 through which to introduce the guide wire 57. In other words, this balloon catheter 50 is a so-called rapid exchange type catheter. Note that the balloon catheter may be an over-the-wire type catheter.

Figure 3:
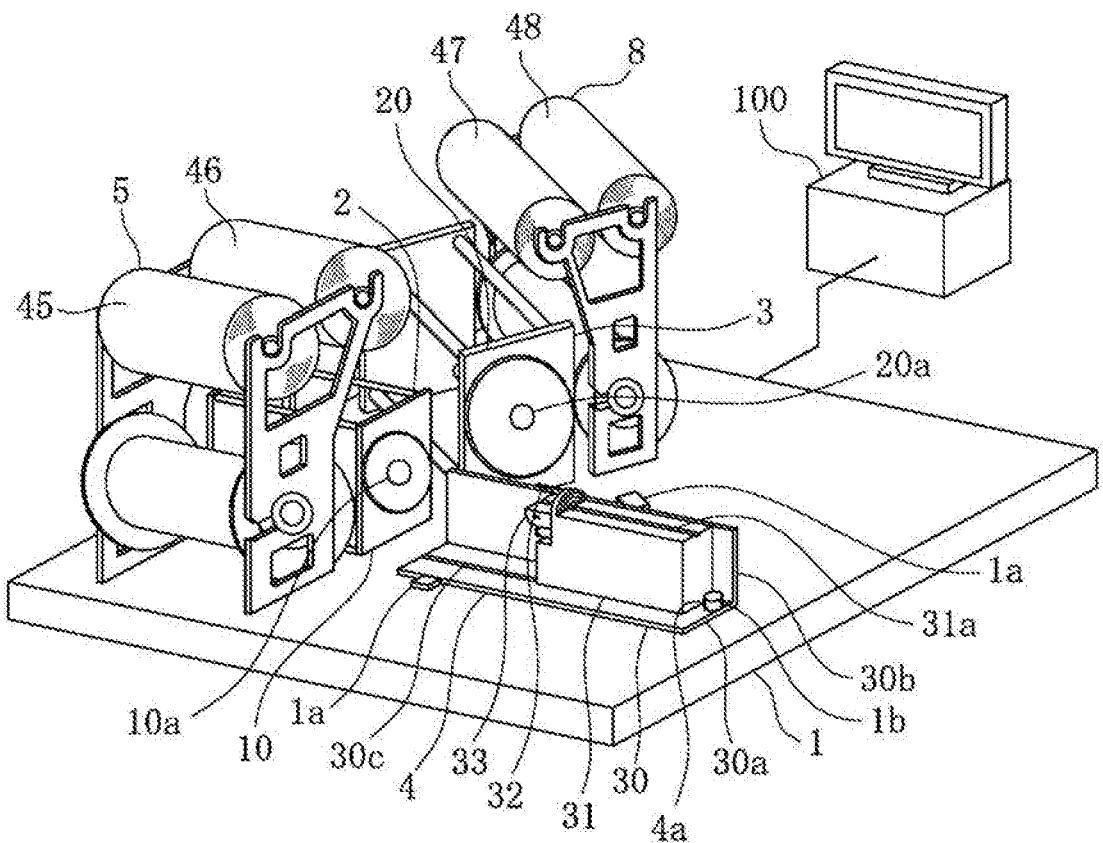
FIG. 3 is a perspective view of a balloon wrapping apparatus according to the present embodiment.

In the next place, the balloon wrapping apparatus will be described. As depicted in FIG. 3, the balloon wrapping apparatus includes a base 1 formed in a base shape, a pleating section 2, a folding section 3, a support base 4, and a control unit 100. The pleating section 2 is capable of forming a balloon 52 with wing shapes projecting in radial directions. The folding section 3 is capable of folding the wing shapes formed in the balloon 52 in the manner of laying the wing shapes flat in a circumferential direction. The support base 4 is capable of disposing and holding the balloon catheter 50 thereon. The control unit 100 is, for example, a computer, which supervisingly controls the pleating section 2, the folding section 3 and the support base 4. The wing shapes formed in the balloon 52 are formed of pleats of balloon thin film material having a length extending substantially in a major axis direction of the balloon 52, and are so formed that the pleats project in the circumferential direction from the major axis of the balloon 52, as viewed in a section perpendicular to the major axis of the balloon 52. The length of the wing shapes in the major axis direction does not exceed the length of the balloon 52, and, for example, can be approximately 3 mm to 400 mm, preferably approximately 3 mm to 300 mm, more preferably approximately 30 mm to 300 mm, and further preferably approximately 40 mm to 200 mm. The length by which the wing shape projects in the circumferential direction from the shaft 51 can be 1 mm to 8 mm. The number of the wing shapes is not particularly limited, and can be, for example, selected from among two, three, four, five, six and seven; in the present invention, for example, the number is three and four.

A film supplying section 5 for supplying a first film 45 and a second film 46 to the pleating section 2 is disposed on the base 1, adjacently to the pleating section 2. In addition, a film supplying section 8 for supplying a first film 47 and a second film 48 to the folding section 3 is disposed on the base 1, adjacently to the folding section 3.

The pleating section 2 has a front surface plate 10 perpendicular to the base 1, and the front surface plate 10 has an insertion hole 10a through which a distal portion of the balloon catheter 50 can be inserted. In addition, the folding section 3 has a front surface plate 20 perpendicular to the base 1, and the front surface plate 20 has an insertion hole 20a through which the distal portion of the balloon catheter 50 can be inserted. The front surface plate 20 of the folding section 3 is oriented in a direction different by a predetermined angle from a direction in which the front surface plate 10 of the pleating section 2 is oriented.

In accordance with an exemplary embodiment, the support base 4 is formed, on the side remote from the pleating section 2 and the folding section 3, with a hole 4a in which a support rod 1b projecting upward from the base 1 is pivotally fitted. By being slid on an upper surface of the base 1 with the support rod 1b as a center, the support base 4 can be positioned in a position for facing the front surface plate 10 of the pleating section 2 and in a position for facing the front surface plate 20 of the folding section 3.

In accordance with an exemplary embodiment, two positioning sections 1a capable of positioning the support base 4 to be oriented in two different directions are provided on the base 1. In FIG. 2, the support base 4 is positioned in contact with the positioning section 1a projecting from the base 1, in such a manner as to face the front surface plate 10 of the pleating section 2. The support base 4 can also be positioned such as to face the front surface plate 20 of the folding section 3, by putting the support base 4 in contact with the positioning section 1a on the other side.

The support base 4 includes a base section 30 placed on the base 1, a holding base section 31 which can be moved horizontally on the base section 30, a rotational support portion 33 rotatable in relation to the holding base section 31, and a rotational driving section 35 such as a motor for rotating the rotational support portion 33. The base section 30 can include a bottom surface portion 30a placed on an upper surface of the base 1 and positioned by the positioning section 1a, and a side surface portion 30b extending vertically upward from a side portion of the bottom surface portion 30a. A slide guide portion 30c for guiding a sliding movement of the holding base section 31 toward the pleating section 2 or the folding section 3 is formed at an upper surface of the bottom surface portion 30a.

Figure 4:
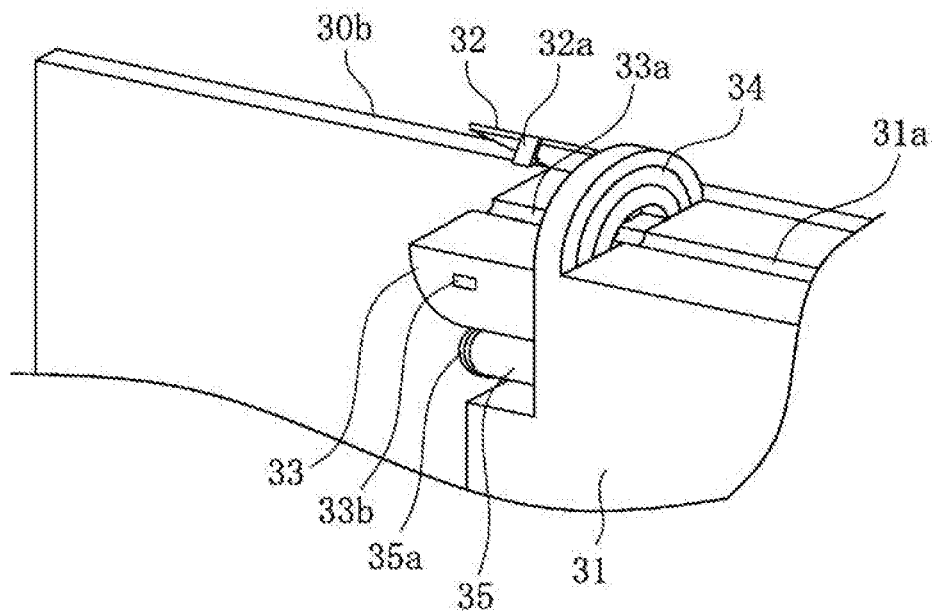
FIG. 4 is an enlarged perspective view of a holding base section of the balloon wrapping apparatus.

As depicted in FIGS. 3 and 4, the holding base section 31 can be formed substantially in the shape of a rectangular parallelepiped which makes contact with the bottom surface portion 30a and the side surface portion 30b of the base section 30, and its lower surface is slidably guided by the slide guide portion 30c of the bottom surface portion 30a. An upper surface of the holding base section 31 has a groove-shaped placing portion 31a on which the shaft 51 of the balloon catheter 50 can be placed. A bearing section 34 is provided on a distal side of an upper surface of the holding base section 31, and the rotational support portion 33 is rotatably interlocked through the bearing section 34. A roller 35a rotationally driven by the rotational driving section 35 provided on the holding base section 31 makes contact with an outer circumferential surface of the rotational support portion 33, and, with the roller 35a rotated, the rotational support portion 33 can be rotated within a range of approximately 180 degrees. Note that the range of the rotational support portion 33 is not particularly limited. The holding base section 31 is formed, on an extension line of the placing portion 31a, with a groove-shaped rotation-side placing portion 33a on which the shaft 51 can be placed. In addition, the holding base section 31 is provided with a holding portion 32 such as to cover the rotation-side placing portion 33a from above. The shaft 51 placed on the rotation-side placing portion 33a can be held and fixed by the holding portion 32. In addition, the holding portion 32 is movably rotationally interlocked with the rotational support portion 33 by a hinge or the like. In addition, the holding portion 32 is formed with an engaging portion 32a which can be engaged with a recess 33b formed in an outer circumferential surface of the rotational support portion 33, and, with the engaging portion 32a engaging the recess 33b, a state in which the shaft 51 is placed on the rotation-side placing portion 33a can be maintained. Note that a flexible material may be disposed at parts of the rotation-side placing portion 33a and the holding portion 32 which parts make contact with the shaft 51, for restraining deformation of the shaft 51. Examples of the flexible material are synthetic resin elastomers such as olefin elastomers (for example, polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), polyurethane, urethane elastomers, and fluoro-resin elastomers, and rubbers such as synthetic rubbers such as urethane rubber, silicone rubbers, and butadiene rubber, and natural rubbers such as latex rubber.

In a state in which the support base 4 faces the front surface plate 10 of the pleating section 2, the center of the insertion hole 10a formed in the front surface plate 10 is located on an extension line of the rotation-side placing portion 33a of the holding base section 31. Therefore, with the holding base section 31 slid on the upper surface of the base section 30, the balloon catheter 50 with the shaft 51 placed on the placing portion 31a is inserted into the inside of the pleating section 2 through the center position of the insertion hole 10a. In a state in which the support base 4 faces the front surface plate 20 of the folding section 3, the center of the insertion hole 20a formed in the front surface plate 20 is located on an extension line of the rotation-side placing portion 33a. Therefore, with the holding base section 31 slid on the upper surface of the base section 30, the balloon catheter 50 with the shaft 51 placed on the rotation-side placing portion 33a is inserted into the inside of the folding section 3 through the center position of the insertion hole 20a.

Figure 5:
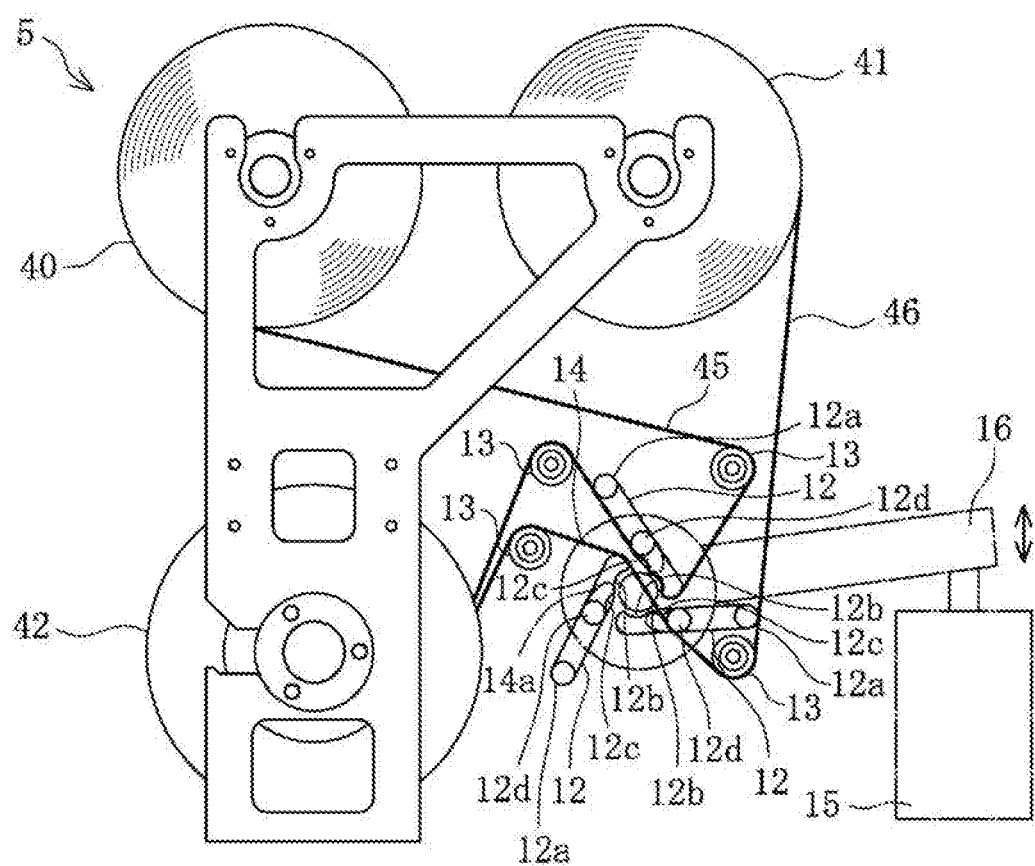
FIG. 5 is a front view depicting the layout of blades of the pleating section and a film supplying section.

Now, the structure of the pleating section 2 will be described below. As illustrated in FIG. 5, the pleating section 2 is provided therein with three blades 12 (wing forming members). Each of the blades 12 is a plate-shaped member which is the same in sectional shape at each position along the axial direction of the balloon catheter 50 inserted. The blades 12 are disposed such that they are, for example, at an angle of 120° from one another, with the center position in regard of insertion of the balloon 52 as a reference. In other words, the blades 12 are disposed at regular angular intervals along the circumferential direction. The blade 12 has a rotational center portion 12a near an outer circumferential end portion thereof, and can be moved rotationally about the rotational center portion 12a. In addition, the blade 12 has a moving pin 12c extending in the axial direction, on the inner circumferential side of the rotational center portion 12a. The moving pin 12c is fitted in a fitting groove 14a formed in a rotary member 14 which is rotatable in the pleating section 2. The rotary member 14 is interlocked with a beam portion 16 extending substantially horizontally. The rotary member 14 is movable rotationally by receiving a rotating force from the beam portion 16 which is inclined by receiving a force from a drive source 15 such as a hydraulic cylinder or a motor. When the rotary member 14 is rotated, the moving pins 12c fitted in the fitting grooves 14a are moved in the circumferential direction, whereby each of the blades 12 is moved rotationally about the rotational center portion 12a. With the three blades 12 moved rotationally, a space region in a central area surrounded by the blades 12 can be narrowed. Note that the number of the blades 12 need only be two or more, and is not particularly limited.

In accordance with an exemplary embodiment, the blade 12 has a first shape forming portion 12b and a second shape forming portion 12c which are substantially arcuate in shape, at inner circumferential end portions on the side opposite to the rotational center portion 12a. Attendant on rotary movement of the blade 12, the first shape forming portion 12b makes contact with the surface of the balloon 52 inserted in the pleating section 2, whereby the balloon 52 can be formed with wing shapes. Attendant on rotary movement of the blade 12, the second shape forming portion 12c makes contact with the wing portion formed in the balloon 52, whereby the wing shape can be curved in a predetermined direction. In addition, the pleating section 2 has a heater (not depicted) for heating the blades 12. Note that the blades 12 may have a function of cooling. In accordance with an exemplary embodiment, the length of the blade 12 along the axial direction of the balloon catheter 50 is greater than the length of the balloon 52. In addition, the lengths of the first shape forming portion 12b and the second shape forming portion 12c of the blade 12 may or may not range over the whole length of the blade 12.

In accordance with an exemplary embodiment, the blades 12 are supplied with the first film 45 and the second film 46 which are formed of resin, from the film supplying section 5. For guiding each of the films 45, 46, a plurality of rotary shaft portions 13 are provided in the pleating section 2. The first film 45 is supplied from a first film holding section 40 and through the rotary shaft portion 13 to be fed to a surface of the blade 12 disposed at an upper part. In addition, the first film 45 is fed through the blade 12 and the rotary shaft portion 13 to reach a film take-up section 42 which is rotationally driven by a drive source (not depicted) such as a motor. The second film 46 is supplied from a second film holding section 41 and through the rotary shaft portion 13 to be fed to the two blades 12 disposed at lower parts. In addition, the second film 46 is fed through the rotary shaft portion 13 to reach the film take-up section 42. As a result of these, a center position of the pleating section 2 in which the balloon 52 is inserted is in the state of being surrounded by the first film 45 and the second film 46.

The first film 45 and the second film 46 have a protecting function for preventing direct contact of the balloon 52 with the surfaces of the blades 12 when the balloon 52 is inserted into the pleating section 2 and the blades 12 are moved rotationally to form the balloon 52 with wing shapes. After the wing shapes of the balloon 52 are formed, predetermined lengths of the first film 45 and the second film 46 are taken up by the film take-up section 42. In other words, the portions of the first film 45 and the second film 46 which portions have once made contact with the balloon 52 do not make contact with the balloon 52 again, and new portions of the films are supplied to the center position of the pleating section 2 every time the balloon 52 is inserted.

Figure 7:
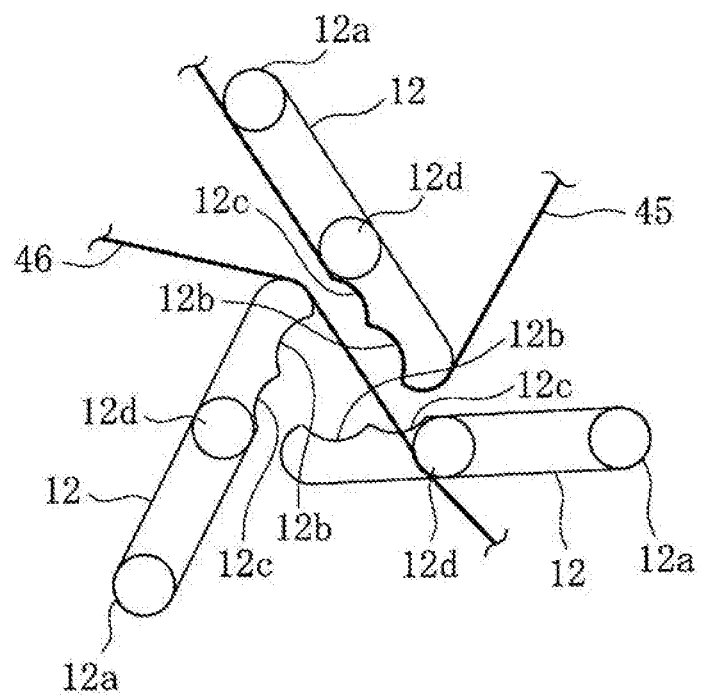
FIG. 7 is a front view of the blades in the pleating section.

As depicted in FIG. 7, in a state before insertion of the balloon 52, the first shape forming portions 12b and the second shape forming portions 12c of the three blades 12 are in the state of being spaced from one another. A central region between the blades 12 is surrounded by the substantially arcuate first shape forming portions 12b, and the balloon 52 yet to be wrapped can be inserted therein.

In forming the balloon 52 with wing shapes, first, the shaft 51 of the balloon catheter 50 is placed on the placing portion 31a of the holding base section 31 and the rotation-side placing portion 33a of the rotational support portion 33, and is held on the rotational support portion 33 by the holding portion 32. The inflation fluid is injected into the balloon 52 through a three-way cock (valve) attached to the hub 56, the hub 56 and the inner tube 54, whereby the balloon 52 is put into a state of being inflated to a certain extent. The core metal member 6 is inserted into the guide wire lumen 65. By the core metal member 6, the shaft 51 is restrained from bending due to its own weight. As a result, the balloon 52 can be accurately positioned in a desired position. In addition, the blades 12 in the pleating section 2 are heated. In addition, with the core metal member 6 inserted in the guide wire lumen 65, crushing of the shaft 51 at the holding portion 32 can be restrained.

The core metal member 6 is formed in a thin elongated wire-like shape or a hollow shape from a metallic material. As the metallic material for forming the core metal member 6, there is selected a material having such a degree of hardness that with the core metal member 6 inserted in the balloon 52 and the shaft 51, a distal portion of the shaft 51 inclusive of the balloon 52 is prevented from bending due to its own weight. The metallic material for forming the core metal member 6 is not specifically restricted, and examples thereof include stainless steel, Ni—Ti alloys, tungsten, and hard metals. In addition, the core metal member 6 may be formed by annealing any of these metallic materials, to realize a shape memory property.

The core metal member 6 is formed in a substantially circular shape in section, and an outside (outer) diameter of the core metal member 6 is equal to an inside (inner) diameter of the inner tube 54 or smaller than the inside diameter, for example, by 0.01 mm to 0.1 mm. If the outside diameter of the core metal member 6 is smaller than the aforesaid appropriate value in relation to the inside diameter of the inner tube 54, the balloon 52 part cannot be held sufficiently by the core metal member 6, and bending of the balloon 52 would occur. As a result, the shaft 51 may be distorted when the balloon 52 is formed with wing shapes by the pleating section 2. In accordance with an exemplary embodiment, if the outside diameter of the core metal member 6 is greater than the aforesaid appropriate value in relation to the inside diameter of the inner tube 54, the core metal member 6 may interfere with the inner surface of the inner tube 54, possibly breaking the inner tube 54. With the outside diameter of the core metal member 6 set as above-mentioned, these problems can be prevented from occurring.

Figure 6:
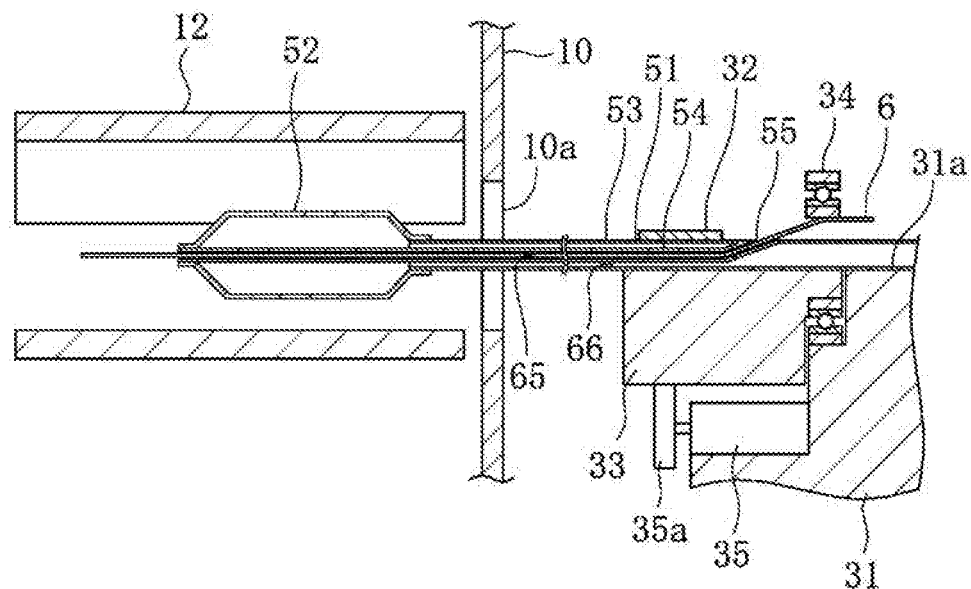
FIG. 6 is a sectional view depicting the balloon catheter disposed in the pleating section.

Next, as depicted in FIG. 6, the holding base section 31 is moved on an upper surface of the base section 30, whereby the balloon 52 is inserted into the pleating section 2. In this instance, since the core metal member 6 is inserted in the guide wire lumen 65, the shaft 51 is restrained from bending due to its own weight, and the balloon 52 can be accurately positioned in the center position of the pleating section 2.

Figure 8:
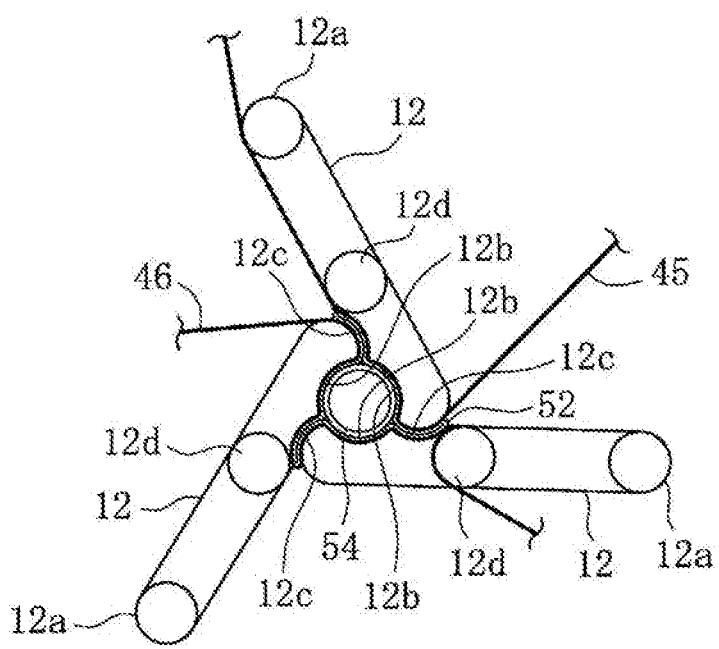
FIG. 8 is a front view of the blades in a state in which the blades are moved rotationally from the state of FIG. 7 to form a balloon with wing shapes.

Next, the rotary member 14 is rotated by operating the drive source 15, whereon the blades 12 are moved rotationally, the first shape forming portions 12b of the blades 12 come closer to one another, and the central region between the blades 12 is narrowed, as depicted in FIG. 8. Attendant on this, the balloon 52 inserted in the central region between the blades 12 is pressed against the inner tube 54 by the first shape forming portions 12b. A portion of the balloon 52 which portion is not pressed by the first shape forming portion 12b is pushed out into a gap between a distal portion of one blade 12 and the second shape forming portion 12c of the blade 12 adjacent to the one blade 12, whereby a wing shape curved to one side is formed. Since the balloon 52 is heated by the blades 12, the wing shapes thus formed can be maintained in their shape. In this way, the balloon 52 is formed with three wing shapes in the circumferential direction. Note that in the case where the surface of the balloon 52 is provided thereon with a coating which is weak to heat, the blades 12 may not necessarily be heated, or may be cooled.

In accordance with an exemplary embodiment, in this instance, surfaces of the blades 12 which surfaces make contact with the balloon 52 are covered with the first film 45 and the second film 46, so that the balloon 52 does not make direct contact with the surfaces of the blades 12. After the balloon 52 is formed with the wing shapes, the blades 12 are moved rotationally in the manner of being returned into their original positions, and the balloon 52 is withdrawn from the pleating section 2. Note that in the process of pleating, a step of excessively inflating the balloon 52 and then deflating the balloon 52 a little or a step of inflating the balloon 52 while avoiding excessive inflation and then deflating the balloon 52 a little may be provided.

Now, the structure of the folding section 3 will be described below. As illustrated in FIG. 9, the folding section 3 is provided therein with ten blades 22 (folding members). In accordance with an exemplary embodiment, each of the blades 22 is a plate-shaped member formed to be the same in sectional shape at each position along the axial direction of the balloon catheter 50 to be inserted. In accordance with an exemplary embodiment, the blades 22 can be disposed such that they are, for example, at an angle of 36° from one another, with the center position in regard of insertion of the balloon as a reference. In other words, the blades 22 are disposed at regular angular intervals along the circumferential direction. The blade 22 has a rotational center portion 22a near a substantial center thereof, and can be moved rotationally about the rotational center portion 22a. In addition, the blade 22 has a moving pin 22c extending in the axial direction, near a substantially outer circumferential end portion thereof. The moving pin 22c is fitted in a fitting groove 23a formed in a rotary member 23 which is rotatable in the folding section 3. The rotary member 23 is interlocked with a beam portion 25 extending substantially horizontally. The rotary member 23 is movable rotationally by receiving a rotating force from the beam portion 25 which is inclined by receiving a force from a drive source 24 such as a hydraulic cylinder or a motor. When the rotary member 23 is rotated, the moving pins 22*c* fitted in the fitting grooves 23*a* are moved in the circumferential direction, whereby each of the blades 22 is moved rotationally about the rotational center portion 22*a*. With the ten blades 22 moved rotationally, a space region in a central area surrounded by the blades 22 can be narrowed. Note that the number of the blades 22 is not particularly limited.

In accordance with an exemplary embodiment, the blade 22 can be bent on the distal side, and has a distal portion 22*b* in a pointing (or pointed) shape. Attendant on rotary movement of the blade 22, the distal portion 22*b* makes contact with a surface of the balloon 52 inserted in the folding section 3, whereby the wing shape formed in the balloon 52 can be folded in the manner of lying flat in the circumferential direction. In addition, the folding section 3 has a heater (not depicted) for heating the blades 22. Note that the blades 22 may have a function of cooling.

The blades 22 are supplied with a first film 47 and a second film 48 from a film supplying section 8. In accordance with an exemplary embodiment, the film supplying structure is the same as in the case of the pleating section 2. The first film 47 and the second film 48 are disposed opposite to each other in such a manner as to sandwich a central space region surrounded by the blades 22. By the first film 47 and the second film 48, the balloon 52 inserted in the folding section 3 can be prevented from making direct contact with the surfaces of the blades 22. The first film 47 and the second film 48 are fed through the blades 22, to reach a film take-up section 49 which is rotationally driven by a drive source (not depicted) such as a motor.

After the balloon catheter 50 is inserted into the pleating section 2 and the balloon 52 is formed with the wing shapes as aforementioned, the holding base section 31 is moved on an upper surface of the base section 30 to be thereby spaced from the pleating section 2, and to withdraw the balloon catheter 50 from the pleating section 2. Next, the support base 4 is moved by sliding on the upper surface of the base 1, and the support base 4 is positioned in such a position as to face the front surface plate 20 of the folding section 3. Thereafter, the holding base section 31 is moved on the upper surface of the base section 30, to insert the balloon catheter 50 into the folding section 3. Note that the blades 22 in the folding section 3 are heated. In addition, the blades 22 may not necessarily be heated, or may be cooled. In this instance, as depicted in FIG. 10, the shaft 51 is maintained in the state of being held by the holding portion 32 of the support base 4. In addition, since the core metal member 6 is inserted in the balloon catheter 50, bending of the balloon catheter 50 due to its own weight is restrained, so that the balloon 52 can be accurately positioned and inserted into the center position of the folding section 3.

Figure 11:
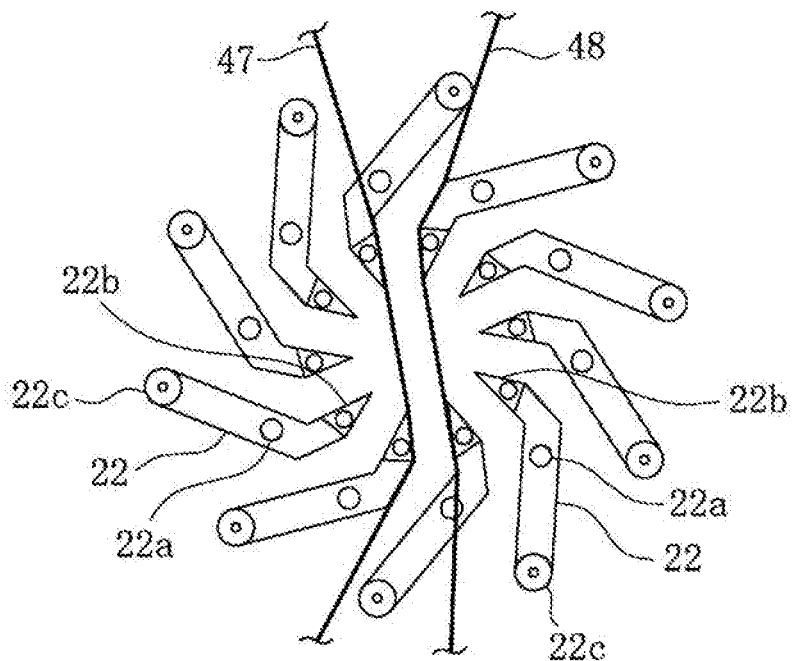
FIG. 11 is a front view of the blades in the folding section.

As depicted in FIG. 11, in a state before insertion of the balloon 52, the distal portions 22*b* of the blades 22 are in the state of being spaced from one another in a circumferential direction. The balloon 52 formed with the wing shapes can be inserted into a central region which is surrounded by the blades 22 and which is between the first film 47 and the second film 48.

Figure 12:
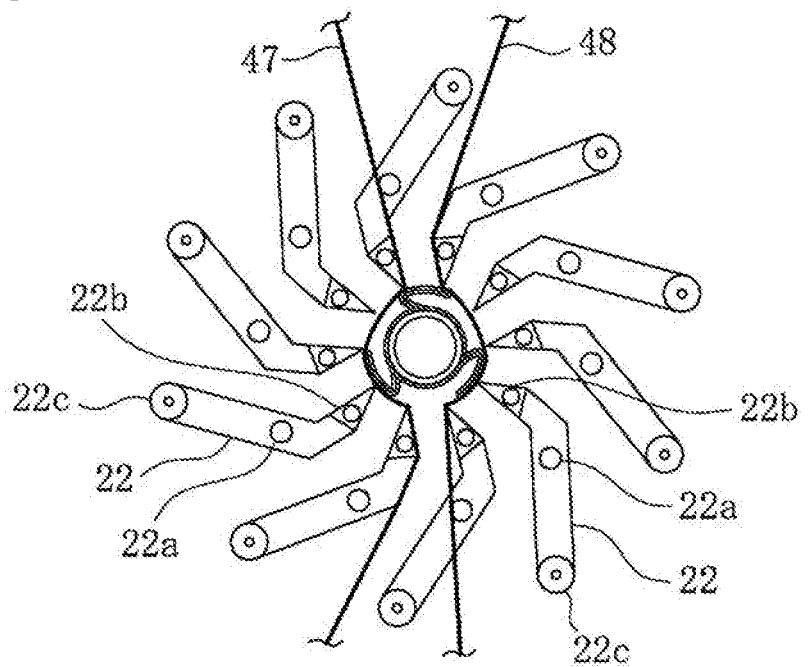
FIG. 12 is a front view of the blades in a state in which the blades have been moved rotationally from the state of FIG. 11 to make contact with wing shapes of a balloon.
Figure 13:
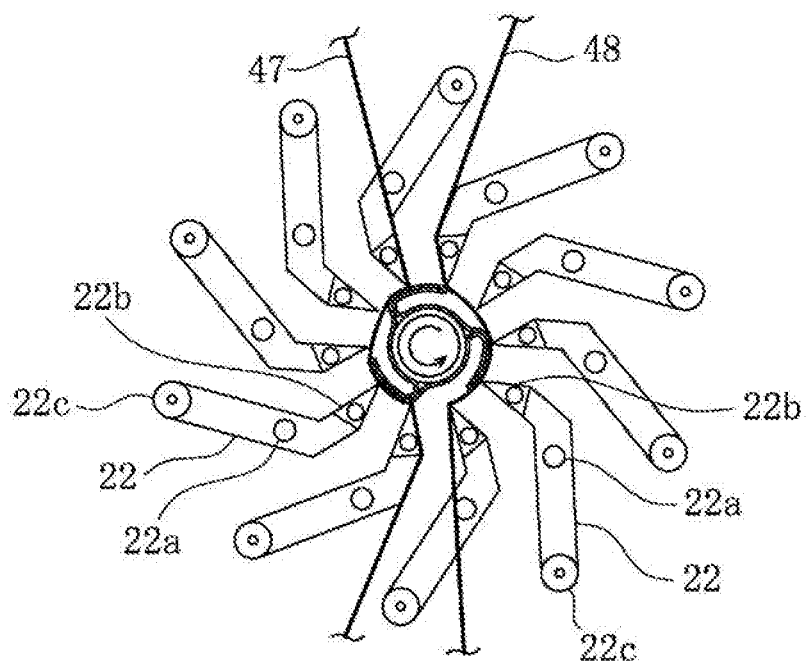
FIG. 13 is a front view of the blades in a state in which the balloons have been rotated from the state of FIG. 12.

When the balloon 52 formed with the wing shapes is inserted in the folding section 3, the balloon 52 is disposed between the first film 47 and the second film 48, as depicted in FIG. 12. Next, the drive source 24 is operated to rotate the rotary member 23 by a predetermined angle, whereon the blades 22 are moved rotationally as depicted in FIG. 13, the distal portions 22*b* of the blades 22 come closer to one another, and the central region between the blades 22 is narrowed. Attendant on this, the distal portions 22*b* of the blades 22 make good contact with the wing shapes of the balloon 52, through the first film 47 and the second film 48.

Subsequently, the rotational driving section 35 is operated by the control unit 100, to rotate the rotational support portion 33 within a range, for example, of 180 degrees. The rotating direction of the rotational support portion 33 is reverse to the rotary movement direction of the blades 22. As a result of this, the balloon 52 in contact with the distal portions 22*b* of the blades 22 is also rotated, and the inclination directions of the wing shapes of the balloon 52 are unified into one direction.

Figure 14:
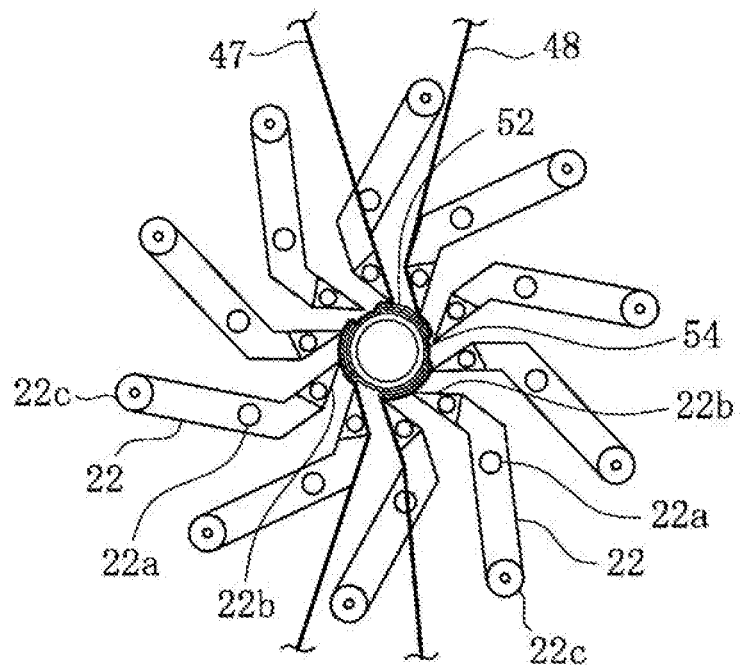
FIG. 14 is a front view of the blades in a state in which the blades have been moved rotationally from the state of FIG. 13 to fold wing shapes of a balloon in a circumferential direction.

Next, the drive source 24 is operated to rotate the rotary member 23 further, whereon the blades 22 are moved rotationally, the distal portions 22*b* of the blades 22 come closer to one another, and the central region between the blades 22 is narrowed further, as illustrated in FIG. 14. Attendant on this, the balloon 52 inserted in the central region between the blades 22 is put into a state in which the wing shapes are laid flat in the circumferential direction by the distal portions 22*b* of the blades 22. In this instance, since the inclination directions of the wing shapes of the balloon 52 are unified, beforehand or by the rotation of the balloon 52 during the rotary movement of the blades 22, wrapping of the wing shapes of the balloon 52 in the reverse direction (back folding) can be restrained from being generated. In addition, since the blades 22 are preliminarily heated before insertion of the balloon 52 and the balloon 52 is heated by the blades 22, the wing shapes laid flat in the circumferential direction by the blades 22 can maintain their shape. Note that the blades 22 may be preliminarily cooled.

In this instance, that surface of each blade 22 which makes contact with the balloon 52 is covered with the first film 47 and the second film 48, so that the balloon 52 does not make direct contact with the surfaces of the blades 22. After the wing shapes of the balloon 52 are folded, the blades 22 are moved rotationally in such a manner as to return into their original positions. Next, the balloon 52 is withdrawn from the folding section 3, and the holding of the shaft 51 by the holding portion 32 is released, whereon the wrapping of the balloon 52 of the balloon catheter 50 is completed.

While a case in which the balloon 52 of a rapid exchange type catheter is wrapped by the balloon wrapping apparatus has been described hereinabove, a balloon 52 of an over-the-wire type catheter can also be wrapped by the same balloon wrapping apparatus.

As has been described above, the balloon wrapping apparatus according to the present embodiment is a balloon wrapping apparatus for wrapping a balloon 52 of a balloon catheter 50 provided with the balloon 52 at a distal portion of an elongated shaft 51, and includes: the pleating section 2 that forms the balloon 52 with wing shapes projecting in radial directions; the folding section 3 that has a plurality of blades 22 (folding members) aligned in the circumferential direction, and that folds the wing shapes formed in the balloon 52 along the circumferential direction by moving rotationally the blades 22; and the rotational support portion 33 that supports a part of the shaft 51 which part is on the proximal side of the balloon 52, and that rotates the shaft 51 in the direction opposite to the rotary movement direction of the blades 22 in a state in which the balloon 52 is positioned in relation to the folding section 3.

The balloon wrapping apparatus configured as above has the rotational support portion 33 that rotates the shaft 51 in the direction opposite to the rotary movement direction of the blades 22. Therefore, it is possible to rotate the balloon 52 and thereby to align the orientations of the wing shapes into one direction. For this reason, the directions in which the wing shapes are folded in the folding section 3 are stabilized, generation of back folding can be restrained, and the balloon 52 can be wrapped appropriately.

In addition, since the rotational support portion 33 has the holding portion 32 for holding the shaft 51, it is possible to hold the shaft 51 and to stably rotate the shaft 51. For this reason, generation of back folding in the folding section 3 can be restrained more securely, and the balloon 52 can be wrapped appropriately.

In addition, where the balloon wrapping apparatus has the core metal member 6 to be inserted in the shaft 51, the shaft 51 rotated by the rotational support portion 33 can be restrained from bending, and the rotation can be stabilized. Therefore, the balloon 52 can be wrapped appropriately.

In addition, the present disclosure also includes the balloon wrapping method. The balloon wrapping method is a balloon wrapping method for wrapping a balloon 52 of a balloon catheter 50 provided with the balloon 52 at a distal portion of an elongated shaft 51, and includes: a step of forming the balloon 52 with wing shapes projecting in radial directions; a step of disposing the balloon 52 formed with the wing shapes in a central area of a plurality of blades 22 aligned in a circumferential direction and putting the blades 22 into contact with the wing shapes of the balloon 52; a step of rotating the shaft 51 in a direction reverse to a rotary movement direction of the blades 22; and a step of moving rotationally the blades 22 to fold the wing shapes formed in the balloon 52 along the circumferential direction.

In the balloon wrapping method configured as above, the shaft 51 is rotated in the direction reverse to the rotary movement direction of the blades 22, and, further, the blades 22 are moved rotationally, to fold the wing shapes of the balloon 52. Therefore, the orientations of the wing shapes can be aligned in one direction. For this reason, the directions in which the wing shapes are folded by the blades 22 are stabilized, generation of back folding can be restrained, and the balloon 52 can be wrapped appropriately.

In addition, where the blades 22 are moved rotationally and the blades 22 are thereby put into contact with the wing shapes of the balloon 52 in the step of putting the blades 22 into contact with the wing shapes of the balloon 52, the blades 22 can be reliably put into contact with the wing shapes of the balloon 52. For this reason, at the time of rotating the shaft 51 in the direction reverse to the rotary movement direction of the blades 22 in the subsequent step, the orientations of the wing shapes of the balloon 52 can be aligned more assuredly.

Note that the present disclosure is not limited only to the aforementioned embodiment, and various modifications can be made by those skilled in the art within the technical thought of the present disclosure. For example, while the wing shapes formed in the balloon 52 are folded along the circumferential direction by rotating the shaft 51 in the direction reverse to the rotary movement direction of the blades 22, then stopping the rotation and thereafter moving rotationally the blades 22 in the aforementioned embodiment, the wing shapes formed in the balloon 52 may be folded along the circumferential direction by moving rotationally the blades 22 while rotating the shaft 51 in the direction reverse to the rotary movement direction of the blades 22. With such a configuration, the directions in which the wing shapes are folded by the blades 22 are stabilized reliably, so that generation of back folding can be securely restrained, and the balloon 52 can be wrapped appropriately.

In addition, while the wing shapes formed in the balloon 52 are put into contact with the blades 22 by moving rotationally the blades 22 by a predetermined angle in the aforementioned embodiment, the blades 22 may not necessarily be moved rotationally so long as the wing shapes formed in the balloon 52 can be put into contact with the blades 22.

Figure 15A:
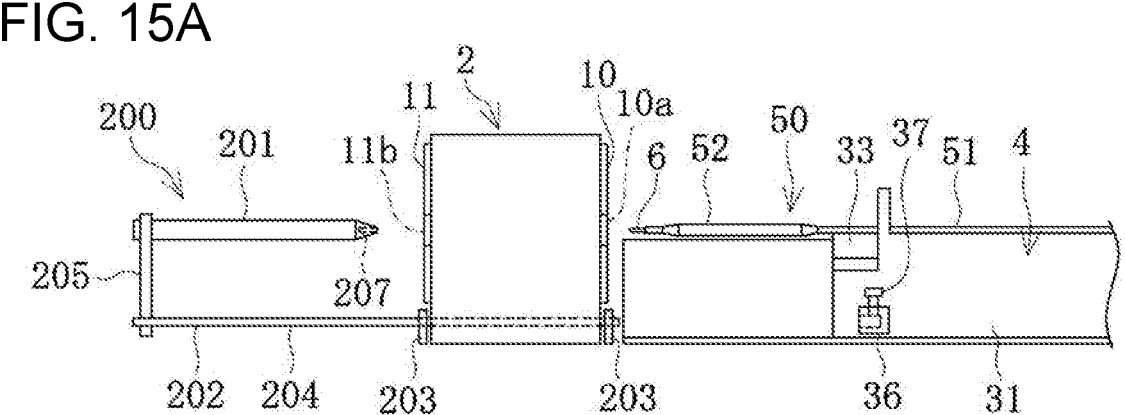
FIGS. 15A-15C are side views of a pleating section according to another embodiment.

Now, a pleating section 2 according to another embodiment will be described below. As illustrated in FIG. 15A, the pleating section 2 according to a third mode is provided with an insertion assisting section 200 for assisting the insertion of the balloon catheter 50 into the insertion hole 10a. The insertion assisting section 200 can be interlocked with the holding base section 31 that holds the shaft 51 of the balloon catheter 50. The insertion assisting section 200 includes an elongated assisting shaft 201, an interlock portion 202 for interlocking the assisting shaft 201 and the holding base section 31, and a support portion 203 for supporting the interlock portion 202 in a slidable manner. The interlock portion 202 includes an elongated interlock shaft 204, and a fixing portion 205 for fixing the assisting shaft 201 and the interlock shaft 204.

One end of the interlock shaft 204 is fixed to the assisting shaft 201 by the fixing portion 205. The other end of the interlock shaft 204 abuts on, and is interlockable with, a holding base side interlock portion 36 of the holding base section 31. The holding base side interlock portion 36 has, for example, a fixing screw 37 for fixing the assisting shaft 201.

The assisting shaft 201 is formed at a distal portion thereof with a cavity portion 207 into which the core metal member 6 to be inserted in the balloon catheter 50 can be inserted. With the core metal member 6 inserted in the cavity portion 207, the balloon catheter 50 can be restrained from bending. Note that the assisting shaft 201 can also hold the shaft 51 of the balloon catheter 50. The assisting shaft 201 can enter a back surface hole 11a provided in the pleating section 2 on the side opposite to the insertion hole 10a, and can protrude from the insertion hole 10a to the exterior.

Figure 15B:
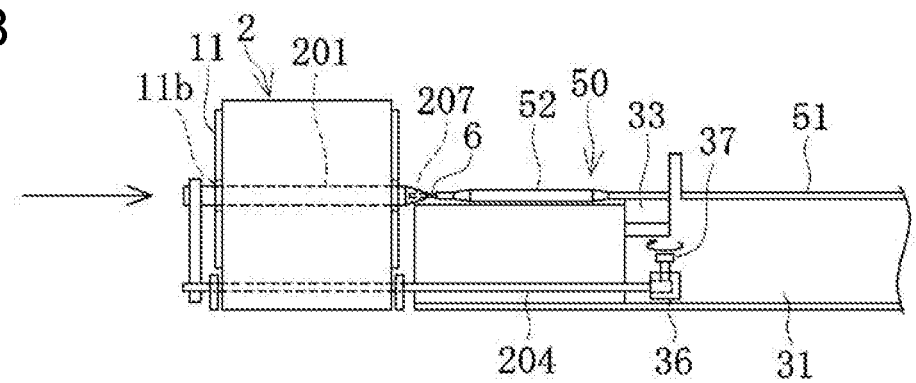
Figure 15C:
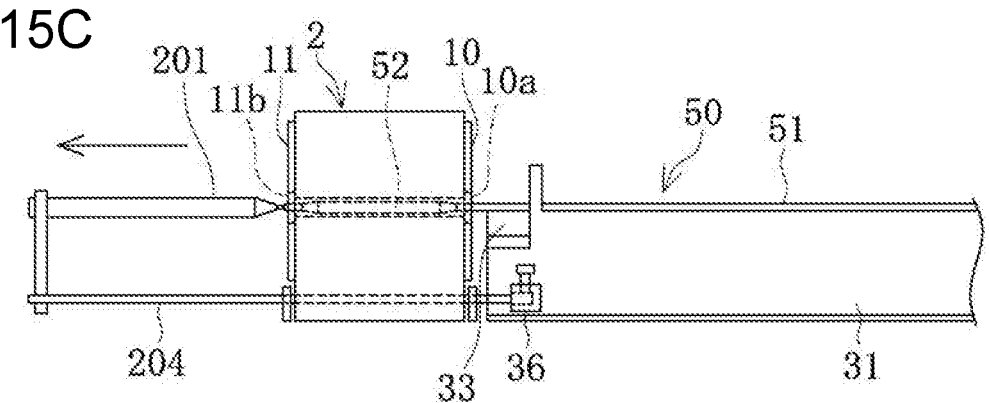

In inserting the balloon catheter 50 into the pleating section 2, the assisting shaft 201 is inserted into the back surface hole 11a of the pleating section 2 and is protruded from the insertion hole 10a, as depicted in FIG. 15B. Next, the core metal member 6 is inserted into the cavity portion 207 of the assisting shaft 201, and the interlock shaft 204 is fixed to the holding base section 31. Thereafter, as depicted in FIG. 15C, the holding base section 31 is moved toward the pleating section 2, whereon the balloon catheter 50 is inserted through the insertion hole 10a into the inside of the pleating section 2. In this instance, the assisting shaft 201 is also moved together with the holding base section 31, and, therefore, the balloon 52 can be inserted into a central area of the blades 12 of the pleating section 2 while a state of the balloon 52 being held by the assisting shaft 201 is maintained. As a result of this, the balloon 52 can be accurately positioned, and inserted, in relation to the pleating section 2. Note that the insertion assisting section 200 may be provided in the folding section 3.

In addition, the aforementioned assisting shaft may be provided with a mechanism for clamping and fixing the core metal member 6 and the shaft 51. The mechanism for clamping and fixing the core metal member 6 and the shaft 51 can be, for example, a collet chuck, a scroll chuck, a drill chuck, or an independent chuck.

EXAMPLES

Examples of the present invention and Comparative Examples will be described below. Drug-coated balloons of Examples 1 to 7 and Comparative Examples 1 to 6 were produced under the conditions set forth in Tables 1 to 3 (FIGS. 16-18).

Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock (valve) was attached to a hub portion of a balloon catheter (material of balloon: nylon, the surface being smooth and non-porous) 2.0 mm in diameter and 40 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire (solid) 0.39 mm in diameter and 700 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to a holding base section and a rotational support portion by a holding portion fitted with silicone rubber. In this instance, the three-way cock of the hub of the balloon catheter was attached to an air injection and suction mechanism for inflating and deflating the balloon of the wrapping apparatus. The core metal member protruding from a distal portion of the balloon catheter was inserted into a distal support (assisting shaft) of a pleating section 2. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Comparative Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 4.0 mm in diameter and 200 mm in length when inflated, the balloon was inflated at 4 atm, and coating with the coating liquid was slowly conducted such that the amount of paclitaxel on the balloon would be approximately 3.6 µg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Comparative Example 2

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 3.0 mm in diameter and 200 mm in length when inflated, the balloon was inflated at 4 atm, and coating with the coating liquid was slowly conducted such that the amount of paclitaxel on the balloon would be approximately 3.6 µg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 2

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Comparative Example 3

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 6.0 mm in diameter and 200 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 3

(1) Production of Drug-Coated Balloon

In the same procedure as in the production example of the drug-coated balloon in Example 1, a drug-coated balloon of a balloon catheter (material of balloon: nylon, the surface being smooth and non-porous) 6.0 mm in diameter and 200 mm in length was produced.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward by 5 mm and was fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, a collet chuck affixed to a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having eight blades. After the balloon was pushed in completely, the position of the distal support was fixed, and the support base section with the shaft of the balloon catheter fixed thereto was pulled backward by 5 mm and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The eight blades were held in a closed state for a while, after which the blades were slowly opened, to spread the first film and the second film, and the balloon was drawn back from the folding section.

Example 4

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward by 5 mm, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward by 5 mm and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first films, and the balloon was drawn back from the folding section.

Example 5

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward with a force of 5 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the distal support was fixed, and the support base section with the shaft of the balloon catheter fixed thereto was pulled backward by a force of 5 N and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 6

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 7

(1) Production of Drug-Coated Balloon

In the same procedure as in the production example of the drug-coated balloon in Example 1, a drug-coated balloon of a balloon catheter (material of balloon: nylon, the surface being smooth and non-porous) 3.0 mm in diameter and 20 mm in length was produced.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first film and the second film. Thereafter, the balloon was drawn back from the folding section.

Comparative Example 4

(1) Production of Drug-Coated Balloon

In the same procedure as in the production example of the drug-coated balloon in Example 1, a drug coated balloon of a balloon catheter (material of balloon: nylon, the surface being smooth and non-porous) 4.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Comparative Example 5

(1) Production of Drug-Coated Balloon

In the same procedure as in the production example of the drug-coated balloon in Example 1, a drug-coated balloon of a balloon catheter (material of balloon: nylon, the surface being smooth and non-porous) 3.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Comparative Example 6

(1) Production of Drug-Coated Balloon

In the same procedure as in the production example of the drug-coated balloon in Example 1, a drug-coated balloon of a balloon catheter (material of balloon: nylon, the surface being smooth and non-porous) 2.0 mm in diameter and 200 mm in length was produced.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section and the rotational support portion by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into, and fixed to, a collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Measurement of Amount of Paclitaxel Remaining on Balloon After Folding

For the drug-coated balloons produced in Examples 1 and 2 and Comparative Examples 1 to 5, the amount of paclitaxel remaining on the balloon was measured in the following procedure.

(1) Method

The drug-coated balloon after folding was immersed in a methanol solution, followed by shaking by use of a shaker for 10 minutes, to extract paclitaxel present in the coating on the balloon. The light absorbance, at 227 nm, of the methanol solution into which paclitaxel had been extracted was measured by high-speed liquid chromatography using an ultraviolet-and-visible absorptiometer, and the amount of paclitaxel per balloon ([μg/balloon]) was determined. Further, from the amount of paclitaxel thus obtained and the surface area of the balloon, the amount of paclitaxel per unit area of balloon ([μg/mm$^2$]) was calculated.

(2) Results

In Table 4 (FIG. 19), the amount of paclitaxel (theoretical value) on the balloon upon coating and the amount of paclitaxel (measured value) on the balloon after folding are depicted as amount per unit area. In addition, retention rate of paclitaxel after folding was calculated by dividing the amount of paclitaxel on the balloon after folding by the amount of paclitaxel on the balloon upon coating, and multiplying the quotient by 100.

As depicted in Table 4 (FIG. 19), in every one of Examples 1 and 2 and Comparative Examples 1 to 3, the retention rate of paclitaxel was high. In Comparative Examples 4 and 5, the retention rate of paclitaxel was as low as less than 80%. Note that the films were used in the pleating and folding in Examples 1 and 2 and Comparative Examples 1 to 3, but films were not used in the pleating and folding in Comparative Examples 4 and 5. It could be confirmed that detachment of the drug coating layer can be reduced by using films in pleating and folding.

Evaluation of Generation of Back Folding Upon Folding

For the drug-coated balloons prepared under the conditions of Example 2 and Example 6, the generation rate of back folding upon folding was evaluated.

(1) Method

The wrapping direction of wings of the drug-coated balloons upon folding was observed on a digital microscope. In the case where the wrapping directions of the wings were not in one direction and there was the wings whose wrapping direction was reverse to the normal direction, the case was counted as back folding.

(2) Results

Table 5 depicts the number of drug-coated balloons in which back folding was generated, the total number of drug-coated balloons subjected to folding, and generation rate of back folding. The generation rate of back folding was calculated by dividing the number of drug-coated balloons in which back folding was generated by the total number of drug-coated balloons subjected to folding, and multiplying the quotient by 100.

As depicted in Table 5 (FIG. 20), in the method of Example 2 in which the balloon was rotated during folding, back folding was scarcely generated. In the method of Comparative Example 6 in which the balloon was not rotated during folding, back folding was generated in approximately one half of the samples subjected to folding. Accordingly, it could be confirmed that the rotation of the balloon during folding has an effect to reduce the generation of back folding.

The detailed description above describes a balloon wrapping apparatus and balloon wrapping method for wrapping a balloon of a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon wrapping method for wrapping a balloon of a balloon catheter provided with the balloon at a distal portion of an elongated shaft, the balloon wrapping method comprising:
   forming the balloon with wing shapes projecting in radial directions;
   supplying a plurality of folding members with a first film and a second film, the first film and the second film being disposed opposite to each other in such a manner as to sandwich a central space region surrounded by each of the plurality of folding members;
   disposing the balloon formed with the wing shapes at a central area of a plurality of folding members aligned in a circumferential direction and putting surfaces of the folding members into contact with the wing shapes of the balloon, and wherein the surfaces of the folding members making contact with the balloon are covered with the first film and the second film;
   moving the folding members rotationally to fold the wing shapes formed in the balloon along the circumferential direction while rotating the shaft in a direction reverse to a rotary movement direction of the folding members; and
   moving rotationally the folding members to fold the wing shapes formed in the balloon along the circumferential direction.

2. The balloon wrapping method according to claim 1, wherein in the putting of the surfaces of the folding members into contact with the wing shapes of the balloon, the method further comprising:
   rotationally moving the folding members to put the folding members into contact with the wing shapes of the balloon.

3. The balloon wrapping method according to claim 1, further comprising:
   maintaining the position of the elongated shaft with a holding portion of a rotational support portion.

4. The balloon wrapping method according to claim 1, further comprising:
   inserting a core metal member in the elongated shaft to restrain bending of the balloon catheter.

5. The balloon wrapping method according to claim 1, further comprising:
   putting the surfaces of the folding members into contact with the wing shapes of the balloon by rotating the folding members; and
   covering the surfaces of the folding members making contact with the balloon with the first film and the second film.

6. The balloon wrapping method according to claim 1, wherein each of the plurality of folding members is a plate-shaped member having a same sectional shape at each position along an axial direction of the balloon catheter, and each of the plurality of folding members being disposed such that the plurality of folding members are at an angle of 36° from one another.

7. The balloon wrapping method according to claim 1, further comprising:
   disposing each of the plurality of folding members at regular angular intervals along the circumferential direction.

8. The balloon wrapping method according to claim 3, further comprising: disposing a pleating section and a folding section comprising the plurality of folding members on a base and orienting each of the pleating section and the folding section in a different direction by a predetermined angle from each other.

9. The balloon wrapping method according to claim 8, further comprising:
   arranging the rotational support portion on a pivotable support base; and
   arranging the distal portion of the elongated shaft positionable in relation to the pleating section and the folding section with the pivotable support base.

10. The balloon wrapping method according to claim 1, further comprising: preventing direct contact of the balloon and surfaces of the folding members with the first film and the second film.

* * * * *